(12) United States Patent
Foley

(10) Patent No.: US 8,548,757 B1
(45) Date of Patent: *Oct. 1, 2013

(54) METHOD FOR CALCULATING MAXIMUM ALLOWABLE OPERATING PRESSURE AND MAXIMUM OPERATING PRESSURE OF A PIPELINE

(71) Applicant: RCP Inc., Houston, TX (US)

(72) Inventor: Christopher Brian Foley, Houston, TX (US)

(73) Assignee: RCP Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/741,259

(22) Filed: Jan. 14, 2013

(51) Int. Cl.
*G01F 1/28* (2006.01)

(52) U.S. Cl.
USPC .................... 702/50; 702/33; 702/34; 702/35

(58) Field of Classification Search
USPC ...................... 702/33–35, 47, 50, 51; 700/28, 700/32, 46; 705/412, 413; 137/1, 2, 12, 137/13, 486, 488; 73/700, 861.01, 861.04, 73/861.71
See application file for complete search history.

(56) References Cited

U.S. PATENT DOCUMENTS

| | | | |
|---|---|---|---|
| 4,707,797 A | 11/1987 | Briggs | |
| 7,366,621 B2 | 4/2008 | Sprague | |
| 7,414,395 B2 | 8/2008 | Gao et al. | |
| 7,426,942 B2 * | 9/2008 | Rice | 138/99 |
| 7,643,974 B2 | 1/2010 | Harper et al. | |
| 7,647,136 B2 | 1/2010 | McDowell | |
| 7,668,688 B2 | 2/2010 | Najim Al-Khamis | |
| 7,835,893 B2 | 11/2010 | Cullick et al. | |
| 7,860,669 B2 | 12/2010 | Najim Al-Khamis | |
| 7,895,052 B1 | 2/2011 | Theriot et al. | |
| 7,895,134 B2 | 2/2011 | Theriot et al. | |
| 7,936,259 B1 | 5/2011 | Weibel et al. | |
| 7,983,853 B2 | 7/2011 | Wang et al. | |
| 8,073,637 B2 | 12/2011 | Cline et al. | |
| 8,155,893 B2 | 4/2012 | Cline et al. | |
| 2006/0065320 A1 * | 3/2006 | Borland et al. | 138/99 |
| 2009/0193899 A1 * | 8/2009 | Panetta et al. | 73/622 |
| 2010/0222911 A1 * | 9/2010 | Castelijns et al. | 700/104 |
| 2011/0137704 A1 * | 6/2011 | Mitra et al. | 705/7.28 |

OTHER PUBLICATIONS

NEMEC, Richard, "PG&E's Pipeline System: From Hell and Back". Pipeline & Gas Journal. Apr. 2013, vol. 240; No. 4.

* cited by examiner

*Primary Examiner* — Sujoy Kundu
(74) *Attorney, Agent, or Firm* — Buskop Law Group, PC; Wendy Buskop

(57) ABSTRACT

A method for providing MAOP information for gas pipelines and MOP for hazardous liquid pipelines that is accessible continuously via a network. The method comprises obtaining a route identifier for a specific pipeline segment; collecting authenticated pipeline segment information related to the specific pipeline segment; collecting non-authenticated pipeline segment information related to the specific pipeline segment; calculating smart segmentation for the specific pipeline segment; identifying gaps in MAOP or MOP data based on the smart segmentation; filling the gaps in MAOP or MOP data; calculating MAOP or MOP for the specific pipeline; and showing valid and invalid MAOP to a user using an executive dashboard.

15 Claims, 8 Drawing Sheets

| Step | No. |
|---|---|
| OBTAINING AN IDENTIFIER FOR A SPECIFIC PIPELINE SEGMENT | 200 |
| COLLECTING AUTHENTICATED PIPELINE SEGMENT INFORMATION | 202 |
| COLLECTING NON-AUTHENTICATED PIPELINE SEGMENT INFORMATION | 204 |
| PERFORMING "DYNAMIC SEGMENTATION" | 206 |
| SORTING THE COLLECTED RECORDS | 207 |
| PERFORMING SMART SEGMENTATION ON THE DYNAMIC SEGMENTED DATA SET FORMING A CALCULATOR INPUT SET | 209 |
| FILLING IN THE CALCULATOR INPUT SET FORMING A RESULTING CALCULATOR INPUT SET | 210 |
| CALCULATING RECORD BY RECORD MAOP OR MOP FORMING A MAOP OR MOP OUTPUT SET | 212 |
| DISPLAYING VALID AND INVALID MAOP OR MOP CALCULATIONS ON AN EXECUTIVE DASHBOARD | 214 |
| DEPICTING A LINEAR REFERENCE PROFILE ON THE EXECUTIVE DASHBOARD | 215 |
| CREATING MULTIPLE USER ACCOUNTS PER PIPELINE OPERATOR | 220 |
| USING MULTIPLE FORMATS OF AUTHENTICATED AND NON-AUTHENTICATED DATA WITH EACH COLLECTING STEP OF AUTHENTICATED AND NON-AUTHENTICATED DATA | 222 |
| USING AN ENCRYPTION MODULE CONTROLLING ACCESS TO THE MAOP OR MOP OUTPUT SET | 224 |
| MAINTAINING THE PIPELINE INFORMATION IN A CLOUD BASED SERVER | 226 |
| CREATING AN AUDITABLE TRACE BETWEEN AUTHENTICATED MAOP OR MOP INPUT DATA AND THE SOURCE DOCUMENTS USING A UNIQUE IDENTIFIER | 228 |
| PROVIDING GOVERNMENT REGULATORY CITATIONS THAT WERE USED TO FORM THE MAOP OR MOP OUTPUT SET | 230 |
| PROVIDING A REPORT OR ALARM TO A USER OF A MAJOR DISCREPANCY WITH MAOP OR MOP OUTPUT SET COMPARED TO A PIPELINE OPERATOR ESTABLISHED MAOP OR MOP | 232 |
| PROVIDING THE MAOP OR MOP OUTSET SET TO THE EXECUTIVE DASHBOARD TO DETERMINE IF A PIPELINE IS CAPABLE OF A HIGHER OPERATING PRESSURE RATING THAN CURRENTLY BEEN ESTABLISHED | 234 |

FIGURE 2

| | |
|---|---|
| OBTAINING AN IDENTIFIER FOR A SPECIFIC PIPELINE SEGMENT | 200 |
| COLLECTING AUTHENTICATED PIPELINE SEGMENT INFORMATION | 202 |
| COLLECTING NON-AUTHENTICATED PIPELINE SEGMENT INFORMATION | 204 |
| PERFORMING "DYNAMIC SEGMENTATION" | 206 |
| SORTING THE COLLECTED RECORDS | 207 |
| PERFORMING SMART SEGMENTATION ON THE DYNAMIC SEGMENTED DATA SET FORMING A CALCULATOR INPUT SET | 208 |
| FILLING IN THE CALCULATOR INPUT SET FORMING A RESULTING CALCULATOR INPUT SET | 210 |
| CALCULATING RECORD BY RECORD MAOP OR MOP FORMING A MAOP OR MOP OUTPUT SET | 212 |
| DISPLAYING VALID AND INVALID MAOP OR MOP CALCULATIONS ON AN EXECUTIVE DASHBOARD | 214 |
| DEPICTING A LINEAR REFERENCE PROFILE ON THE EXECUTIVE DASHBOARD | 215 |
| CREATING MULTIPLE USER ACCOUNTS PER PIPELINE OPERATOR | 220 |
| USING MULTIPLE FORMATS OF AUTHENTICATED AND NON-AUTHENTICATED DATA WITH EACH COLLECTING STEP OF AUTHENTICATED AND NON-AUTHENTICATED DATA | 222 |
| USING AN ENCRYPTION MODULE CONTROLLING ACCESS TO THE MAOP OR MOP OUTPUT SET | 224 |
| MAINTAINING THE PIPELINE INFORMATION IN A CLOUD BASED SERVER | 226 |
| CREATING AN AUDITABLE TRACE BETWEEN AUTHENTICATED MAOP OR MOP INPUT DATA AND THE SOURCE DOCUMENTS USING A UNIQUE IDENTIFIER | 228 |
| PROVIDING GOVERNMENT REGULATORY CITATIONS THAT WERE USED TO FORM THE MAOP OR MOP OUTPUT SET | 230 |
| PROVIDING A REPORT OR ALARM TO A USER OF A MAJOR DISCREPANCY WITH MAOP OR MOP OUTPUT SET COMPARED TO A PIPELINE OPERATOR ESTABLISHED MAOP OR MOP | 232 |
| PROVIDING THE MAOP OR MOP OUTSET SET TO THE EXECUTIVE DASHBOARD TO DETERMINE IF A PIPELINE IS CAPABLE OF A HIGHER OPERATING PRESSURE RATING THAN CURRENTLY BEEN ESTABLISHED | 234 |

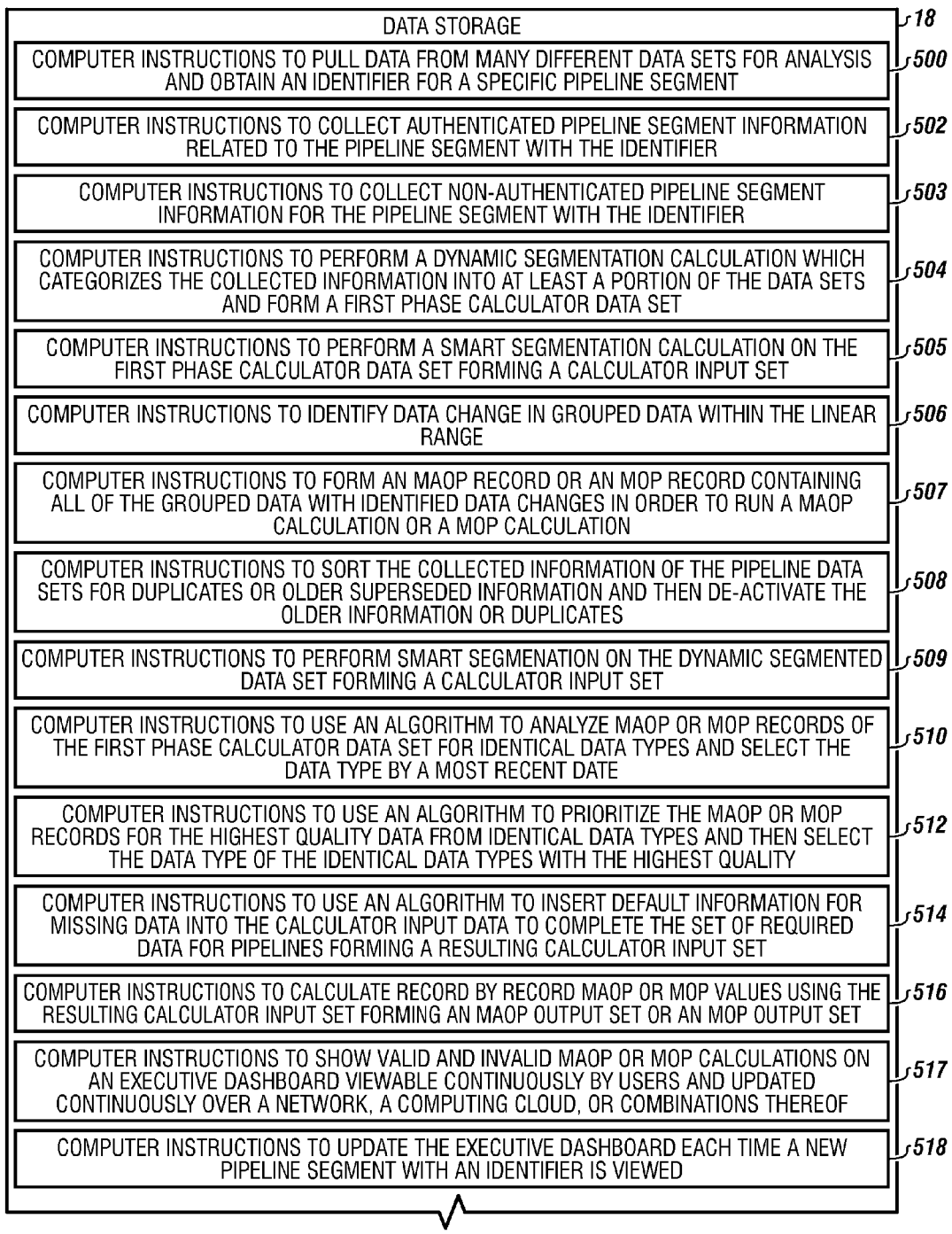

FIGURE 7

| | | | |
|---|---|---|---|
| 700 | LINE LOCATION / STATIONING | | DATA QUALITY GRADE |
| | | | JURISDICTION |
| | | | ASSET TYPE |
| | | | LINE |
| | | | ROUTE |
| | | BEGINNING | SERIES |
| | | | STATION |
| | | | MILEPOST |
| | | | PLUS FOOTAGE |
| | | | MEASURE |
| | | | ELEVATION |
| | | ENDING | SERIES |
| | | | STATION |
| | | | MILEPOST |
| | | | PLUS FOOTAGE |
| | | | MEASURE |
| | | | ELEVATION |
| 702 | CLASS LOCATION | | CLASS DETERMINATION DATE |
| | | | CLASS CHANGE UNDER 192.611 |
| | | | OPERATED AS CLASS 2,3 OR 4 SINCE BEFORE GRANDFATHERED DATE |
| | | | WAIVER ALTERNATIVE MAOP? |
| | | | PREVIOUS CLASS |
| | | | CURRENT CLASS |
| 704 | CONVERTED OR UPRATED | | CONVERTED FROM OTHER SERVICE? |
| | | | UPRATE PRESSURE |
| | | | UPRATED? |
| 706 | OCCUPIED BUILDING WITHIN 300FT | | |
| 708 | MAXIMUM OPERATING TEMPERATURE - °F | | |
| 710 | HIGHEST DOCUMENTED TEST OR OPERATING PRESSURE (FIVE YEAR CODE GRANDFATHER PERIOD) | | |
| 712 | HYDROSTATIC TESTS | | PRESSURE WHEN TESTED TO YEILD (192.619(a)(1)(i)) |
| | | 192 OR 195 COMPLIANT | TEST LENGTH (HOURS) |
| | | | WAS TEST POST-INSTALLATION? |
| | | | TEST DATE |
| | | | TEST PRESSURE |
| | | | ELEVATION OF TEST POINT |
| 714 | PIPE | 780 | DATE INSTALLED |
| | | 781 | DATE OF MANUFACTURE |
| | | 782 ROAD CROSSINGS | ROAD TYPE |
| | | | ROAD INSTALL DATE |
| | | | ROAD DESCRIPTION |
| | | | CASING |
| | | 783 | FABRICATED ASSEMBLY |
| | | 784 | COMPRESSION, REGULATION, MEASURING STATION |
| | | 785 | IS PIPE COLD EXPANDED AND RE-HEATED? |
| | | 786 | MATERIAL |
| | | 787 | O.D. |
| | | 788 | W.T. |
| | | 789 | SEAM TYPE / MANUFACTURING PROCESS 192.113 |
| | | 790 | GRADE |
| 716 | REPAIR SLEEVES | | DATE INSTALLED |
| | | | DATE OF MANUFACTURE |
| | | | FABRICATED ASSEMBLY |
| | | | COMPONENT PRESSURE RATING |
| | | | IS PIPE COLD EXPANDED AND RE-HEATED |
| | | | MATERIAL |
| | | | O.D. |
| | | | W.T. |
| | | | SEAM TYPE / MANUFACTURING PROCESS 192.113 |
| | | | GRADE |
| 718 | ESTABLISHED MAOP (192.611(b) & 192.555(c)) | | |
| 720 | MAXIMUM OPERATING PRESSURE | | MOP |
| | | | MOP DISTRICT |
| 722 | OPERATOR DETERMINED MAOP OVERRIDE | | OVERRIDE CALCULATED MAOP? |
| | | | OVERRIDE DATE |
| | | | MAOP PRESSURE |

US 8,548,757 B1

METHOD FOR CALCULATING MAXIMUM ALLOWABLE OPERATING PRESSURE AND MAXIMUM OPERATING PRESSURE OF A PIPELINE

FIELD

The present embodiments generally relate to a method for calculating the maximum allowable operating pressure or maximum allowable pressure of a pipeline.

BACKGROUND

After a pipeline explosion in San Bruno, Calif. in which eight people perished and approximately fifty houses were damaged or destroyed, the National Transportation and Safety Board (NTSB) investigation and report revealed there was a need for traceable, verifiable and complete MAOP or MOP to prevent this type of accident from occurring in the future.

Part of the reason the pipeline explosion occurred was due to a lack of Maximum Allowable Operating Pressure (MAOP) pipeline information used for gas pipelines and Maximum Operating Pressure (MOP) pipeline information for hazardous liquids (MOP) pushed to groups of users simultaneously that could act.

A need exists for a method for both (i) calculating the MAOP and MOP pipeline information and (ii) pushing that calculated information to groups of users simultaneously, enabling the users to see gaps in the information, enabling users take remedial steps to validate MAOP or MOP which might prevent such accidents in the future.

A further need exists for a method for analyzing the gaps that can occur in design, construction, operation and maintenance data required for Maximum Allowable Operating Pressure (MAOP) pipeline calculations for gas and for Maximum Operating Pressure (MOP) calculations for hazardous liquids, and then identify the type of gap to a plurality of users, simultaneously.

When MAOP and MOP gaps exist, pipelines can explode, killing a lot of people. This method has been needed to prevent these problems.

The present embodiments meet these needs.

BRIEF DESCRIPTION OF THE DRAWINGS

The detailed description will be better understood in conjunction with the accompanying drawings.

FIG. 2 is a diagram of the series of steps of the method.

FIGS. 5A-5C show computer instructions in the data storage according to one or more embodiments.

FIG. 7 is a presentation of the MAOP data fields according to one or more embodiments.

Figure 1:
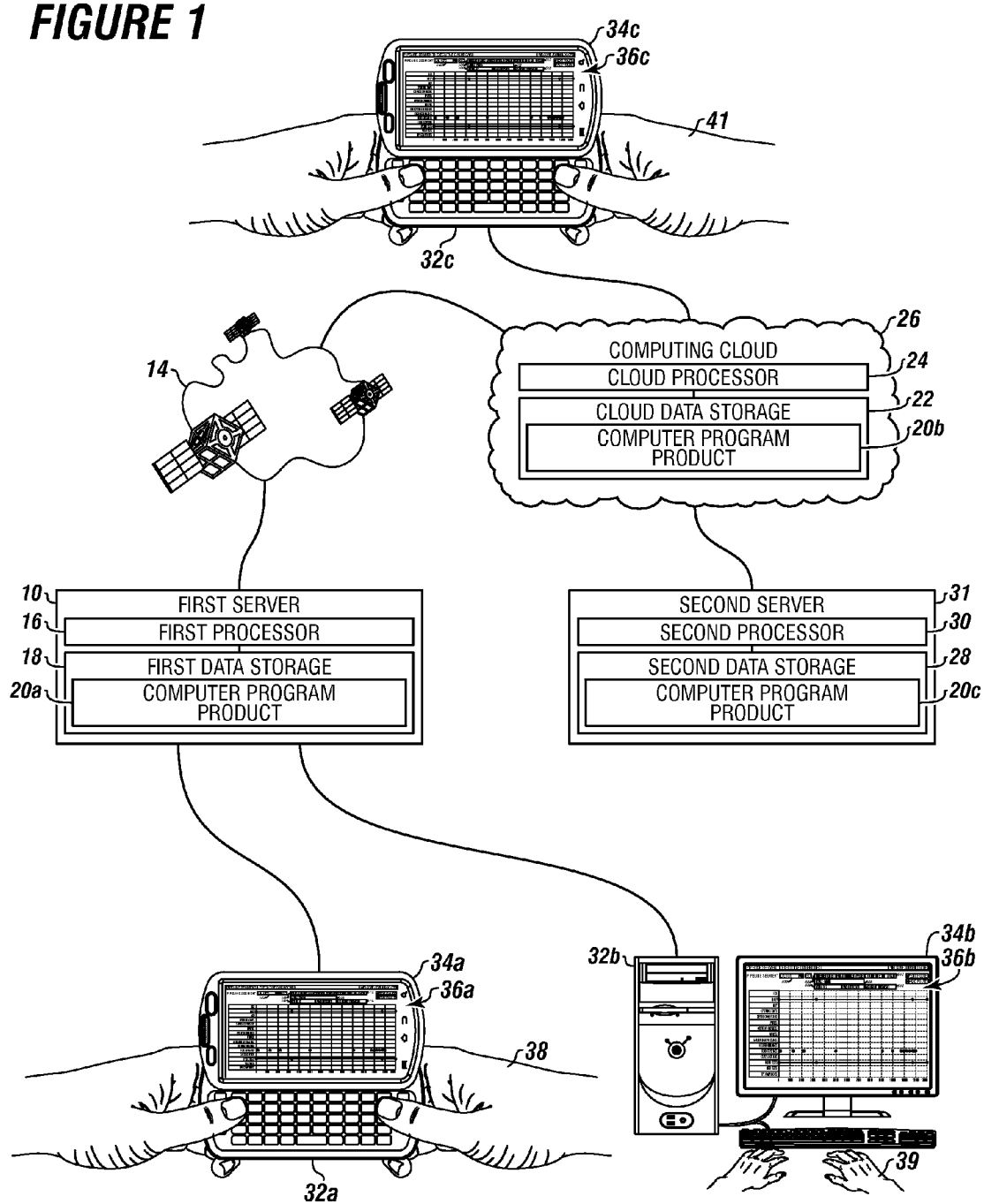
FIG. 1 is an overview of the computer processing equipment used to implement the method.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

The present embodiments generally relate to a method for calculating the maximum allowable operating pressure or maximum allowable pressure of a pipeline.

Various definitions can be used herein in describing the method.

The term "attributes" for a pipeline, as used herein can refer to attributes defined or referred to within 49 CFR part 192 and part 195 and can include as an example, diameter, wall thickness, age, yield strength, seam type, class location, material, pressure tests, date of constructions, and similar specifications as identified in the CFR.

The term "automated" as used herein can refer to a sequence of steps that are undertaken by a processor without the need for human intervention.

The term "computing cloud" as used herein can refer to a computing cloud that is capable of both storing information and performing data functions on information which can be used in the method.

In one or more embodiments, the computing cloud can have at least one processor with at least one data storage that can be operated by a third party and can be accessible from a remote location.

The computing cloud can have a plurality of data storages, which can also be referred to herein as storage devices. The data storage and/or storage devices can be referred to herein collectively as storage units.

The computing cloud can have a plurality of processing units that can be referred to collectively as the processing unit.

The term "continuously" as used herein can refer to accessibility that is viewable 24 hours a day, 7 days a week, and 365 days a year.

The term "gaps in MAOP or MOP data" can refer to missing data, incomplete or data that does not fit within preset limitations for the data of the specific pipeline segment.

The term "gas pipeline" can refer to a pipeline as defined in 49 Code of Federal Regulations (CFR) part 192 as updated August 2012.

The term "grandfather pressure" as used herein is defined in 49 CFR part 192.

The term "hazardous liquid pipeline" can refer to a pipeline as defined in 49 CFR part 195 as updated August 2012.

The term "network" as used herein can refer to a web based communication system which allows local or global communication between client devices and a processor that can be either in a computer cloud or a non-computing cloud server or combinations of servers.

The term "specific pipeline segment" can refer to a certain number of feet or miles of a pipeline that an owner or operator of the pipeline controls. For example, the specific pipeline segment can be a 2 mile pipeline segment of a 500 mile pipeline.

The phrase "traceable, verifiable, and complete MAOP or MOP" can be identical to the terms defined in an advisory bulletin titled "Advisory Bulletin 2012-06 Federal Register Vol. 77, No. 88 Monday, May 7, 2012 pages 26822-26824.

The invention is a method for providing traceable, verifiable and complete Maximum Allowable Operating Pressure (MAOP) information for gas pipelines and for providing traceable, verifiable and complete Maximum Operating Pressure (MOP) information for hazardous liquid pipelines that is accessible continuously via a network.

In one or more embodiments, the method can include the step of obtaining at least one identifier for at least one pipeline segment.

In one or more embodiments, the method can include the step of collecting authenticated pipeline segment information related to the at least one pipeline segment.

The authenticated pipeline segment information can be: physical pipeline attributes; pipeline locations; pipeline testing information; pipeline age and combinations of this information.

In one or more embodiments, the method can include the step of collecting non-authenticated pipeline segment information related to the at least one pipeline segment.

The non-authenticated pipeline segment information can be physical pipeline attributes; pipeline locations; pipeline testing information; pipeline age, and combinations of this information.

In one or more embodiments, the method can include the step of calculating a dynamic segmentation of MAOP or MOP data for each of the pipeline segments forming a dynamic segmented data set.

In one or more embodiments, the method can include the step of calculating a smart segmentation of the dynamic segmented data set forming a calculator input data set.

In one or more embodiments, the method can include the step of identifying and filling in the calculator input data set forming a resulting calculator input set using (i) authenticated information, new non-authenticated information, or combinations thereof, (ii) default values, or (iii) combinations thereof, wherein the default values are provided from one of a plurality of libraries.

The libraries can be: a library of expected physical pipeline attributes; a library of pipeline location information; and a library of testing information for pipelines In one or more embodiments, the method can include the step of performing an MAOP or MOP calculation on a record by record basis using the resulting calculator input set forming a MAOP or MOP output set.

In one or more embodiments, the method can include the step of presenting valid and invalid MAOP or MOP calculations for the MAOP or MOP output set using both (i) graphically valid and invalid MAOP calculations or MOP calculations and (ii) a listing of valid and invalid MAOP calculations or MOP calculations using an executive dashboard viewable 24 hours a day, 7 days a week from a plurality of client devices simultaneously via a network.

The method can enable the invalid MAOP calculations to be presented as a value less than an established MAOP or MOP and the valid MAOP or MOP calculations are presented as a value equal to or greater than an established MAOP or MOP calculation.

The method can include the step of indicating the gaps in MAOP data or MOP data and identifying the gaps visually using graphs and colors to depict the missing data and gaps.

The method can include the step of presenting the MAOP or MOP output set identified in customized reports, standard reports, exception reports, as a Route MAOP Summary report, and as a reports required for regulatory filing.

The method can include the step of presenting the MAOP or MOP output set sorted and viewable by numerical data quality.

The method can include the step wherein any one piece of data can be edited before MAOP or MOP calculation is performed.

The method can include the step of creating multiple user accounts per pipeline operator.

The method can include the step of using multiple formats of authenticated and non-authenticated data.

The method can include the step of using an encryption module to control access to the MAOP or MOP output set.

The method can include the step of storing the pipeline information in a cloud based server.

The method can include the step of permitting a user to manually insert a default value into the MAOP or MOP input data.

The method can include the step of creating an auditable trace between authenticated MAOP or MOP input data and the source documents using a unique identifier.

The method can include the step of providing government regulatory citations that were used to form the MAOP or MOP output set.

The method can include the step of providing a report and/or an alarm to a user of a major discrepancy with MAOP or MOP output set compared to a pipeline operator established MAOP or MOP.

The method can include the step of using the MAOP or MOP outset set to determine if a pipeline is capable of a higher operating pressure rating than currently been established.

The method can include the step of sorting the collected information of the pipeline data sets for duplicates or for older superseded information and de-activating the duplicates and older information prior to performing dynamic segmentation.

Turning now to the Figures, FIG. 1 is an overview of the computer processing equipment used to implement the method.

The computer processing equipment can include a first server 10 connected to a network 14.

The first server 10 can have a first processor 16 and a first data storage 18. The computer instructions, such as a computer program product 20a can operate the system and can reside totally in this first data storage 18 according to one or more embodiments.

In one or more embodiments, the data storage can be non-transitory computer-readable medium. The non-transitory computer-readable medium can be computer-readable media.

In one or more embodiments, a part of the system can include a cloud data storage 22.

In one or more embodiments, a computer program product 20b can operate the system and can partially reside within the cloud data storage 22. Additionally, the cloud data storage 22 can be connected to a cloud processor 24 in a computing cloud 26 that can communicate to the network 14.

In one or more embodiments, a second data storage 28 can be connected to a second processor 30 in a second server 31. A computer program product 20c can reside in the second data storage 28 and operate the system.

The second processor 30 can communicate via the network 14 and can connect to the computing cloud 26, as shown in this Figure.

Client devices 32a, 32b, and 32c can connect to the network 14 to receive the information concerning gaps in MAOP and MOP pipeline information for fast action. Any number of client devices can be used.

Each client device is shown with a display 34a, 34b, and 34c. Executive dashboards 36a, 36b, and 36c can be created by the method and system and shown on the displays 34a, 34b, and 34c.

Users 38, 39, and 41 can all see the same information on the executive dashboards 36a, 36b, and 36c simultaneously, allowing for accelerated, fast action in potentially 2 percent to 25 percent less time concerning the identified gaps.

FIG. 2 is a diagram of the series of steps of the method.

The method can include the step of obtaining an identifier for a specific pipeline segment, as illustrated in box 200.

In an embodiment, the identifier is for at least one pipeline segment connected to a pipeline system controlled by a pipeline operator.

For example, the identifier can be a route identifier such as "LAL1064," the pipeline system can have a title such as "Nine Mile Lateral," and the pipeline operator can have a company name such as "Houston Gas Company."

The method can include the step of collecting authenticated pipeline segment information, as illustrated in box 202.

The authenticated pipeline segment information can relate to the specific pipeline segment and can include physical pipeline attributes, pipeline locations, pipeline testing information, and pipeline age.

For example, authenticated pipeline segment information of physical pipeline attributes can include pipeline design information, such as a pipeline seam type, such as a double submerged arc welded pipe. A similar physical pipeline attribute can be pipeline yield strength of 35,000 PSIG for each segment of the pipeline.

The term "authenticated pipeline segment information" as used herein can refer to information which was obtained from engineers that designed the pipeline, contractors that constructed the pipeline, operators that operated or currently operate and maintain the pipeline, and other professionals, businesses, or governmental entities, that can verify the information is accurate and original.

The term "authenticated pipeline segment information" can also refer to original documents or copies of the original documents, and information contained on those original source documents or copies of those original source documents, which can be verified or authenticated as original, or as a copy of the original. Authenticated pipeline segment information can include original pipeline attributes from construction specifications, purchase orders, materials specification sheets or similar documents.

The method can include the step of collecting non-authenticated pipeline segment information, as illustrated in box 204.

Collecting non-authenticated pipeline segment information can relate to collecting non-authenticated physical pipeline attributes, pipeline locations, pipeline testing information, and pipeline age, which relate to a specific identifier.

The term "non-authenticated pipeline segment information" can refer to information which is not from original documents and information and which is not from copies of original source documents. It can be information from an original source document, but the source of the original document is unknown or highly questionable, such as an unreliable construction document.

Non-authenticated pipeline segment information for pipeline physical attributes can include information that relates to the design, construction, operation and maintenance of the pipeline.

For example, non-authenticated pipeline segment information can be information transposed from an unknown document source into a spread sheet, such as an EXCEL™ spread sheet.

As another example, a piece of non-authenticated pipeline segment information can include information from a pipeline operator's Geographic Information System, such as information on pipeline wall thickness but the source of the wall thickness data is unknown.

The method can include the step of performing dynamic segmentation by the processor, as illustrated in box 206.

In one or more embodiments, the processor can make a dynamic segmentation calculation for the pipeline segment associated with the identifier forming a first phase of the calculator data set.

Dynamic segmentation calculations are performed using multiple MAOP or multiple MOP data types associated with each pipeline segment.

Each data type has its own unique set of linear reference points which indicate changes to that data type along a pipeline segment from one end of the pipeline segment to the other end of the pipeline segment.

The method can include the step of sorting the collected records of the dynamic segmented data set, as illustrated in box 207.

In one or more embodiments, the dynamically segmented data set can be sorted for duplicate information to de-activate the duplicate information, or sorted by date, so that older superseded information is de-activated.

Figure 4:
FIG. 4 shows the steps of performing a smart segmentation calculation according to the method.

The system can perform the step of performing a smart segmentation calculation on the dynamic segmented data set forming a calculator input set, as illustrated in box 208. Details of the smart segmentation calculation are shown in FIG. 4.

The method can include the step of filling in the calculator input set forming a resulting calculator input set, as illustrated in box 210.

In one or more embodiments, the step can include identifying data gaps in the resulting calculator input set and filling in the gaps of the calculator input set forming a resulting calculator input set.

The method can compute gaps in MAOP or MOP data of the calculator input set and then fill those gaps with either (i) new authenticated information, new non-authenticated information, or combinations thereof, (ii) default values, or (iii) combinations thereof, wherein the default values are provided from one of a plurality of libraries.

If MAOP data or MOP data is missing or not collected, then default information is needed.

The method uses an algorithm to insert a default value when no value is provided from either the authenticated pipeline information or the non-authenticated pipeline information.

The default value can be obtained from one or more of a plurality of created libraries formed, populated and updated by an administrator. When the default information is automatically populated from the libraries by the system, the result is termed the resulting calculator input set.

The libraries that supply default values can include a library of expected physical pipeline attributes, a library of pipeline location information, and a library of testing information for pipelines.

The method can pull default information electronically from a plurality of libraries in the data storage.

The libraries can include a library of expected physical pipeline attributes that includes pipe yield, pipe thickness, pipe seam type, and pipe wall strength; a library of pipeline location information including addresses and lengths of pipelines; a library of testing information for pipelines including pressure test results and material test results.

The method can include using the resulting calculator input set for calculating record by record MAOP or MOP forming an MAOP or MOP output set, as illustrated in box 212.

The step for calculating the MAOP or MOP can be performed using a calculation according to the federal rules for MAOP or MOP as found in 49 CFR part 192 and 195, effective in 2012 to take the lowest of the following: (i) design pressure calculations; (ii) hydrostatic test calculations; (iii) highest actual operating pressure preceding an applicable regulatory date found in 49 CFR part 192 or in a similar applicable state regulatory requirement; or (iv) operator determined MAOP resulting in a numeric MAOP value or numerical MOP value for each record of the resulting calculator input set.

The method can include the step of displaying valid and invalid MAOP or MOP calculations on an executive dashboard, as illustrated in box 214. The executive dashboard can be viewable continuously by multiple users from a plurality of client devices simultaneously, wherein the processor updates the executive dashboard continuously for the users.

The method can cause both (i) a graphic depiction of valid and invalid MAOP calculations or MOP calculations and (ii) a listing of valid and invalid MAOP calculations or MOP calculations using the executive dashboard viewable 24 hours a day, 7 days a week from a plurality of client devices simultaneously via a network.

The invalid MAOP calculations are presented as a value less than an established MAOP or MOP and the valid MAOP or MOP calculations are presented as a value equal to or greater than an established MAOP or MOP calculation.

For example, the method can cause the executive dashboard to be updated each time a new pipeline segment with an identifier is viewed.

As another example, the method can cause the executive dashboard to be updated each time a MAOP or MOP calculation is performed.

The method can identify the gaps in MAOP data or MOP data graphically using graphs and colors to depict the missing data including a specific color scheme to identify gaps.

The gaps in MAOP data or MOP data can be inserted into customized reports, standard reports, or other data reports that do not use visual indicators.

In an embodiment, the method can depict a linear referenced profile on the executive dashboard, as illustrated in box 215.

The term "linear referenced profile" can refer to a presentation that shows MAOP or MOP calculations in a line going across a graph that depicts the values across the range of a pipeline segment.

The executive dashboard can show a linear referenced profile to enable viewing of the quality of the data used to calculate the MAOP or MOP value.

In an embodiment, the method can create multiple user accounts per pipeline operator, as illustrated in box 220.

The method can include using multiple formats of authenticated data and non-authenticated data with each collecting step of authenticated and non-authenticated data, as illustrated in box 222.

The method can include using an encryption module to control access to the MAOP or MOP output set, as illustrated in box 224.

The method can include maintaining the pipeline information in a cloud based server, as illustrated in box 226.

The method can include creating an auditable trace between authenticated MAOP or MOP input data and the source documents using a unique identifier, as illustrated in box 228. An example of a unique identifier can be a bar code.

The method can include providing government regulatory citations that were used to form the MAOP or MOP output set, as illustrated in box 230. In one or more embodiments, the government regulatory citations can be state, federal, county, municipal, or combinations thereof.

The method can include providing a report and/or alarm to a user when a major discrepancy with MAOP or MOP output set compared to a pipeline operator established MAOP or MOP exists, as illustrated in box 232.

The method can include providing the MAOP or MOP output set to the executive dashboard to determine if a pipeline is capable of a higher operating pressure rating than has currently been established, as illustrated in box 234.

Figure 3:
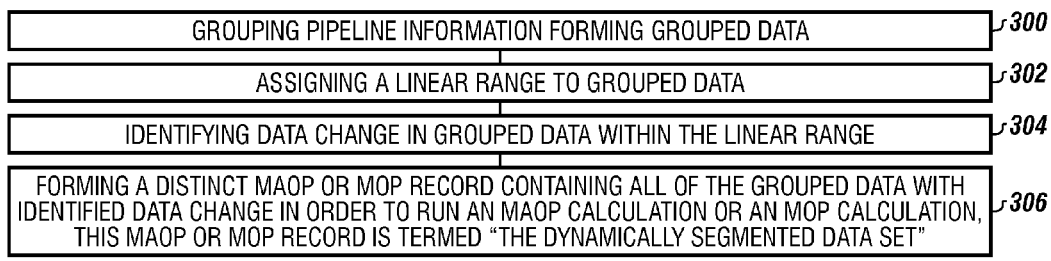
FIG. 3 shows the steps of a dynamic segmentation calculation according to the method.

FIG. 3 shows the steps of a dynamic segmentation calculation according to the method.

The method can include grouping pipeline information forming grouped data, as illustrated in box 300.

For example, all of the data for an identifier can be grouped by data type.

For example, one of the data types can be pipe components and an associated identifier can be "LAL0014".

The method can include assigning a linear range to grouped data, as illustrated in box 302.

The linear range can be formed when the grouped data is associated with distinct physical locations along the pipeline segment. The linear range can have a start point and an end point.

The method can include identifying data change in grouped data within the linear range, as illustrated in box 304.

The term "data change" as used herein can refer to a change in data within a data type.

The method can include forming a distinct MAOP or MOP record containing all of the grouped data with identified data change in order to run an MAOP calculation or an MOP calculation, this MAOP or MOP record is termed "the dynamically segmented data set", as illustrated in box 306.

FIG. 4 shows the steps of performing a smart segmentation calculation according to the method.

A calculator input set is computed from the dynamically segmented data set.

The method can include selecting the most recent data 400 from the dynamically segmented pipeline information.

The method can use an algorithm to analyze MAOP or MOP records of the first phase calculator data set for identical data types and then select the most recent date, that is, for identical data types with multiple dates, the MAOP or MOP data with the most recent date is selected.

The method can include selecting the highest quality data 402 from the most recent data.

The method uses another algorithm to prioritize the MAOP or MOP records for the highest quality data from identical data types and then select the data type of the identical data types with the highest quality forming a calculator input set.

The term "highest quality" as used herein can refer to pipeline data that meets predefined criteria based on a series of criteria, but can also include sources of documents, types of documents, original information, signed and dated documents or transposed original verified information forming a calculator input set.

Figure 5B:
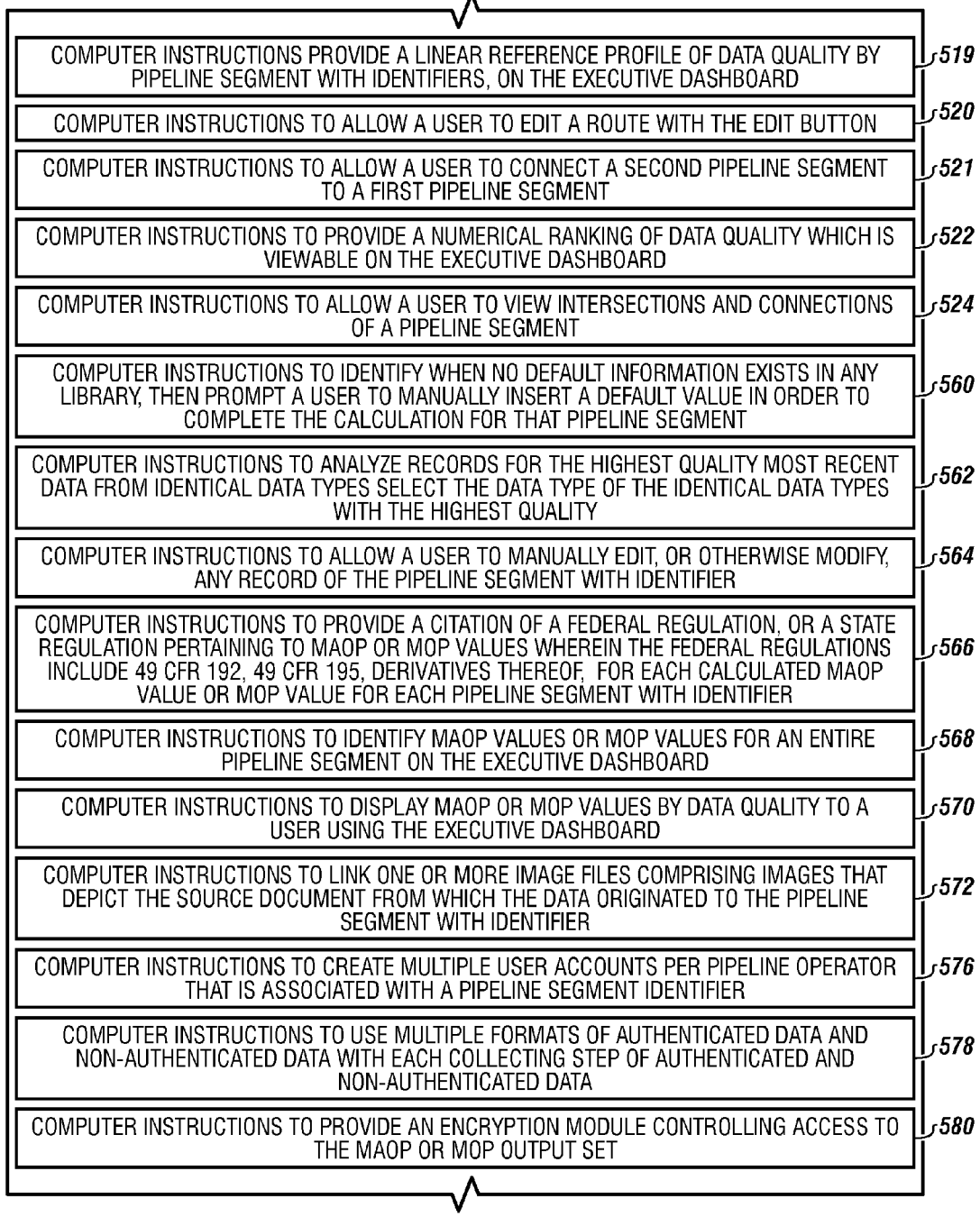
Figure 5C:
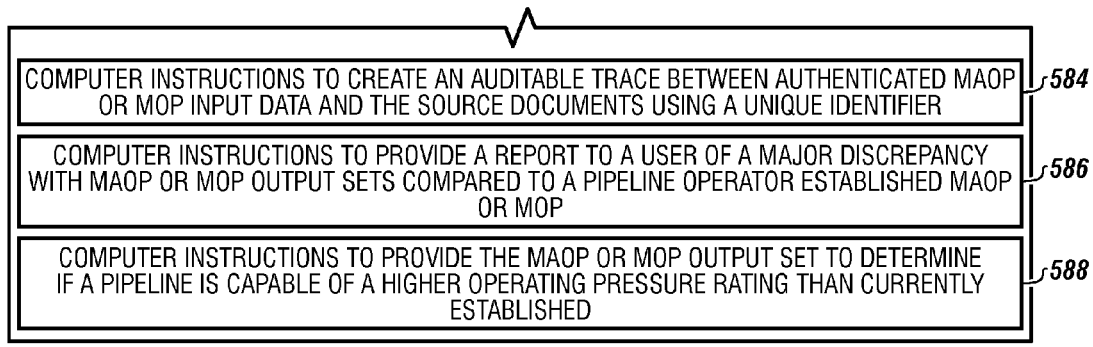

FIGS. 5A-5C show the plurality of computer instructions in the data storage according to one or more embodiments.

The data storage 18 can include computer instructions 500 to pull data from many different data sets for analysis and obtain an identifier for a specific pipeline segment.

The data storage 18 can include computer instructions 502 to collect authenticated pipeline segment information related to the pipeline segment with the identifier.

The data storage 18 can include computer instructions 503 to collect non-authenticated pipeline segment information for the pipeline segment with the identifier.

Each record of the data set contains information from records that can have multiple sets of the same type of data.

All or a portion of these data sets are then used to perform a series of computations that result in a dynamically segmented pipeline data set.

For example, some of the records might have pipeline material used in 1965 and then pipeline material that was changed out in 1990 for the same pipeline segment.

The data storage 18 can include computer instructions 504 to perform a dynamic segmentation calculation which categorizes the collected information into at least a portion of the plurality of data sets and form a first phase calculator data set.

The data storage 18 can include computer instructions 505 to perform a smart segmentation calculation on the first phase calculator data set forming a calculator input set.

These computer instructions can initiate the calculation by grouping information that has been categorized forming grouped data of the calculator input set.

These computer instructions can assign a linear range to grouped data of the calculator input set, wherein each linear range has a start point and an end point.

The data storage 18 can include computer instructions 506 to identify data change in grouped data within the linear range.

The data storage 18 can include computer instructions 507 to form a MAOP or MOP record containing all of the grouped data with identified data changes in order to run a MAOP calculation or a MOP calculation.

This formed MAOP or MOP record is termed herein as "the dynamically segmented data set."

The data storage 18 can include computer instructions 508 to sort the collected information of the pipeline data sets for duplicates or older superseded information and then de-activate the older information or duplicates.

The data storage 18 can include computer instructions 509 to perform smart segmentation on the dynamic segmented data set forming a calculator input set.

The data storage 18 can include computer instructions 510 to use an algorithm to analyze MAOP or MOP records of the first phase calculator data set for identical data types and select the data type by a most recent date.

The data storage 18 can include computer instructions 512 to use an algorithm to prioritize the MAOP or MOP records for the highest quality data from identical data types and then select the data type of the identical data types with the highest quality.

The data storage 18 can include computer instructions 514 to use an algorithm to insert default information for missing data into the calculator input set to complete the set of required data for pipelines forming a resulting calculator input set.

The algorithm pulls default information from the aforementioned plurality of libraries in the data storage, including but not limited to: a library of pipeline location information, a library of pipeline testing information and a library of pipeline attributes.

In an embodiment, the plurality of libraries can be formed, populated and updated by the administrator of the computer instructions to perform the steps of the system or the method.

The libraries can provide default information related to the default value, such as source of the value, similar values for similar by not identically sized pipelines.

One of the libraries used to provide default values can be a library of expected physical pipeline attributes that includes pipe yield, pipe thickness, pipe seam type, and pipe wall strength. Another of the libraries used to providing default values can be a library of pipeline location information. The library can include addresses and lengths of pipelines.

Still another library used to providing default values is a library of testing information for pipeline.

The data storage 18 can include computer instructions 516 to calculate record by record MAOP or MOP values using the resulting calculator input set forming an MAOP output set or an MOP output set.

The data storage 18 can include computer instructions 517 to show valid and invalid MAOP or MOP calculations on an executive dashboard viewable continuously by users and updated continuously over a network, a computing cloud, or combinations thereof.

The data storage 18 can include computer instructions 518 to update the executive dashboard each time a new pipeline segment with an identifier is viewed.

The data storage 18 can include computer instructions 519 to provide a linear reference profile of data quality by pipeline segment with identifiers, on the executive dashboard.

The data storage 18 can include computer instructions 520 to allow a user to edit a route with the edit button.

The data storage 18 can include computer instructions 521 to allow a user to connect a second pipeline segment to a first pipeline segment.

The data storage 18 can include computer instructions to 522 provide a numerical ranking of data quality which is viewable on the executive dashboard.

The data storage 18 can include computer instructions 524 to allow a user to view intersections and connections of a pipeline segment.

The intersections and connections can include types of joints used to connect two different pipeline segments.

The data storage 18 can include computer instructions 560 to identify when no default information exists in any library, then prompts a user to manually insert a default value in order to complete the calculation for that pipeline segment.

The data storage 18 can include computer instructions 562 to analyze records for the highest quality most recent data from identical data types and select the data type of the identical data types with the highest quality.

The term "highest quality most recent data" as used herein can refer to pipeline data that meets a predefined criteria based on a series of criteria that may be user defined, but include source of document, type of document, original information, signed and dated document or transposed information forming a calculator input set.

The data storage 18 can include computer instructions 564 to allow a user to manually edit, or otherwise modify, any record of the pipeline segment with identifier.

In one or more embodiments, the user can edit all or a portion of a pipeline, deleting a pipeline segment, or adding a pipeline segment.

The data storage 18 can include computer instructions 566 to provide a citation of a federal regulation, or a state regulation pertaining to MAOP or MOP values wherein the federal regulations include 49 CFR 192, 49 CFR 195, derivatives thereof, for each calculated MAOP value or MOP value for each pipeline segment with identifier.

The data storage 18 can include computer instructions to 568 identify MAOP values or MOP values for an entire pipeline segment on an executive dashboard.

The data storage 18 can include computer instructions to 570 display MAOP or MOP values by data quality to a user using the executive dashboard.

The term "data quality" can refer to the quality of MAOP or MOP values that meet a predefined acceptability level based on user defined criteria, such as source of data or complimentary source of data. A complimentary source of data can be a second source of a single data point in the MAOP or MOP calculation. For example, pipeline wall thickness can come from a requisition order for pipeline materials as well as from a complimentary source, which can be a pre-construction alignment sheet.

The displayed MAOP values or displayed MOP values can be referred to herein as "a results/output set."

The results/output set can be used for preparing additional SQL server reports such as reports for DOT PHMSA compliance. DOT stands for Department of Transportation and PHMSA stands for Pipeline and Hazardous Materials Safety Administration.

It should be noted that the results/output set can be used for updating one or more of the libraries for the pipeline, such as a pipeline operator's own GIS system.

The data storage 18 can include computer instructions 572 to link one or more image files comprising images that depict the source document from which the data originated to the pipeline segment with identifier.

The data storage can include computer instructions to enable omission of any one piece of data before MAOP or MOP calculation is performed.

The data storage 18 can include computer instructions 576 to create multiple user accounts per pipeline operator that is associated with a pipeline segment identifier.

The data storage 18 can include computer instructions 578 to use multiple formats of authenticated data and non-authenticated data with each collecting step of authenticated and non-authenticated data.

The data storage 18 can include computer instructions 580 to provide an encryption module controlling access to the MAOP or MOP output set.

In one or more embodiments, the data storage can contain computer instructions to maintain the pipeline information in a cloud based server.

The data storage 18 can include computer instructions to create an auditable trace between authenticated MAOP or MOP input data and the source documents using a unique identifier 584.

The data storage 18 can include computer instructions 586 to provide a report to a user of a major discrepancy with MAOP or MOP output sets compared to a pipeline operator established MAOP or MOP.

The data storage 18 can include computer instructions 588 to provide the MAOP or MOP output set to determine if a pipeline is capable of a higher operating pressure rating than currently established.

Figure 6:
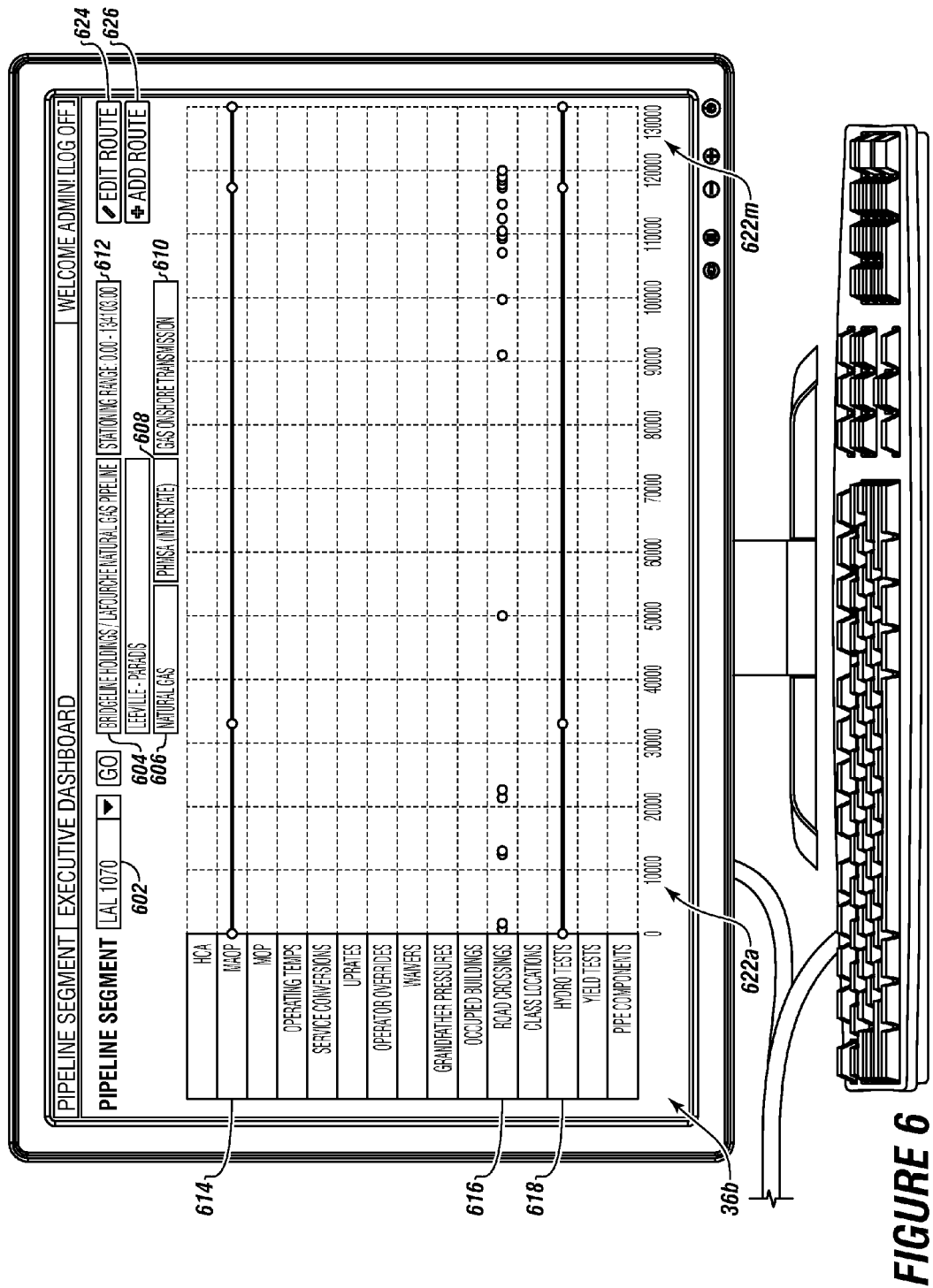
FIG. 6 is an example of a screen shot from the executive dashboard according to one or more embodiments.

FIG. 6 shows a display of an executive dashboard created by the method.

The executive dashboard 36b depicts an identifier 602 for a specific pipeline segment as LAL1070 for a named pipeline 604, the Lafourche Natural Gas Pipeline.

On the executive dashboard 36b can also be other information including type of pipeline 606, "natural gas", jurisdiction of pipeline 608, such as "interstate"; transmission type 610 such as "gas onshore transmission," and stationing range 612, shown in this example as 0.00-134103.00.

FIG. 6 also shows the type of data for this pipeline as MAOP identified as element 614.

The executive dashboard 36b can include information on the location of the pipeline relative to road crossings 616.

The executive dashboard information can include information on pipeline testing information shown as hydro test information 618.

This pipeline is shown having dynamic segments 622a to 622m.

Pipeline dynamic segment 622a for the hydro test 618 has behind it or linked to it a display of the gaps of the MAOP data. Dynamic segment 622a indicates the 10,000 dynamic segment and 622m indicates the 130,000 dynamic segment.

The executive dashboard 36b shows edit button 624. Edit button 624 can connect to computer instructions in the data storage to allow a user to edit a route with the edit button.

The executive dashboard shows an add route button 626.

The add route button 626 can connect to the computer instructions in the data storage to allow a user to connect a second pipeline segment to a first pipeline segment.

The executive dashboard allows a user to view intersections of two different, but connected pipelines while viewing an added pipeline by connecting to the computer instructions to view connections.

FIG. 7 depicts a display of a plurality of pipeline segment information data sets usable with this method.

This Figure further depicts categories of data sets used to compute gaps in the MAOP or MOP. Some of the approximately fifty two different data sets can be related to physical attributes of the pipeline, testing of the pipeline and the physical location of the pipeline.

The data sets can be used to form a first phase calculator data set.

Some the data sets categories are: line location/stationing 700, class location 702, converted or uprated 704, occupied building within 300 feet 706, maximum operating temperature 708, highest documented test or operating pressure including a five year code grandfather period 710, hydrostatic tests 712, pipe information 714, repair sleeves information 716, established MAOP according to 49 CFR part 192.611(B) and part 192.555(B) 718; Maximum Operating Pressure (MOP) 720; and operator Determined MAOP override 722.

Each of these data sets can have various additional data fields. For example, the pipe information 714 can contain, but is not limited to, date installed 780, date of manufacture 781, road crossings 782, fabricated assembly 783, compression regulation, measuring station 784, is pipe cold expanded and re-heated? 785, material 786, outer diameter (O.D) 787, wall thickness (W.T.) 788, seam type 789, and grade 790.

For example, some of the physical attributes can be wall thickness, seam type, yield strength, outside diameter of the pipeline, and material type of the pipeline such as plastic or steel.

Some of the plurality of different data sets can relate to the physical location information can include such as, a longitude and latitude of a road crossing and/or a railroad crossing, class location information which indicates the proximity and density of population to the pipeline including people and buildings.

Age of construction of the pipeline can be one of the many different data sets used in this system.

The data sets can include pressure testing information on the pipeline and may include information on dates of pressure tests, pressures of pressure test, durations of pressure tests, and types of pressure test (whether the pressure test uses water, insert gas, or another gas or liquid). It should be noted that an elevation profile of the pipeline being tested may be one of these data sets.

While these embodiments have been described with emphasis on the embodiments, it should be understood that within the scope of the appended claims, the embodiments might be practiced other than as specifically described herein.

What is claimed is:

1. A method for providing traceable, verifiable and complete Maximum Allowable Operating Pressure (MAOP) information for gas pipelines and for providing traceable, verifiable and complete Maximum Operating Pressure (MOP) information for hazardous liquid pipelines, that is accessible continuously via a network, wherein the method comprises the steps of:
   a. obtaining an identifier for a specific pipeline segment from a list of titles or company name controlled by a pipeline operator, wherein the identifier is obtained using a processor in communication with a non-transitory computer readable medium having computer instructions to obtain an identifier for a specific pipeline segment from a list of titles or company name controlled by a pipeline operator;
   b. collecting authenticated pipeline segment information related to the specific pipeline segment associated with the identifier, using the processor in communication with the non-transitory computer readable medium, wherein the non-transitory computer readable medium further comprises computer instructions to collect authenticated pipeline segment information for the specific pipeline segment associated with the identifier, wherein the authenticated pipeline segment information comprises:
      (i) physical pipeline attributes, wherein the physical pipeline attributes are verified or authenticated as original or as a copy of the original and include original pipeline attributes from construction specifications, purchase orders, materials specification sheets or similar documents originating from engineers that designed the pipeline, contractors that constructed the pipeline, operators that operated or currently operate and maintain the pipeline, each of which verifies that the information is accurate and original;
      (ii) pipeline locations from constructions specifications, purchase orders, materials specification sheets or similar documents originating from engineers that designed the pipeline, contractors that constructed the pipeline, operators that operated or currently operate and maintain the pipeline, each of which verifies that the information is accurate and original;
      (iii) pipeline testing information from constructions specifications, purchase orders, materials specification sheets or similar documents originating from engineers that designed the pipeline, contractors that constructed the pipeline, operators that operated or currently operate and maintain the pipeline, each of which verifies that the information is accurate and original; and
      (iv) pipeline age from constructions specifications, purchase orders, materials specification sheets or similar documents originating from engineers that designed the pipeline, contractors that constructed the pipeline, operators that operated or currently operate and maintain the pipeline, each of which verifies that the information is accurate and original;
   c. collecting non-authenticated pipeline segment information related to the at least one pipeline segment using the processor in communication with the non-transitory computer readable medium, wherein the non-transitory computer readable medium further comprises computer instructions to collect non-authenticated pipeline segment information related to the pipeline segment with the identifier, wherein the non-authenticated pipeline segment information comprises:
      (i) physical pipeline attributes comprising: physical pipeline attributes related to the design, constructions, operation and maintenance of a pipeline, which relate to the identifier;
      (ii) pipeline locations comprising: pipeline locations, which relate to the identifier;
      (iii) pipeline testing information, which relate to the identifier; and
      (iv) pipeline age which relates to the identifier, wherein the non-authenticated pipeline segment information is not from original documents and is not from copies of source documents and can include documents with an unknown source;
   d. performing dynamic segmentation to form a first phase calculator data set using the processor in communication with the non-transitory computer readable medium, wherein the non-transitory computer readable medium further comprises computer instructions to perform dynamic segmentation to categorizes the collected information wherein the dynamic segmentation comprises:
      (i) grouping pipeline information by data type each data type having a unique set of linear reference points that indicate changes to the data type along a pipeline segment forming grouped data;
      (ii) identifying data change within a linear range in the grouped data using a start point and an end point; and
      (iii) forming a dynamically segmented data set comprising a distinct MAOP or MOP record containing all grouped data with identified data changes to run an MAOP calculation or an MOP calculation;
   e. performing smart segmentation on the dynamically segmented data set using the processor in communication with the non-transitory computer readable medium, wherein the non-transitory computer readable medium further comprises computer instructions to perform smart segmentation on the dynamically segmented data set forming a calculator input data set by:
      (i) selecting the most recent data from the dynamically segmented pipeline information;
      (ii) grouping the first phase calculator data set forming grouped data with a linear range; and
      (iii) using an algorithm to analyze MAOP or MOP records of the first phase calculator data set for identical data types then select the most recent date for identical data types with multiple dates; in the linear range;
   f. identifying and filling in the calculator input data set forming a resulting calculator input set using (i) authenticated information, new non-authenticated information, or combinations thereof, (ii) default values, or (iii) combinations thereof, wherein the identifying and filling in the calculator input data set is performed using the processor in communication with the non-transitory computer readable medium, wherein the non-transitory computer readable medium further comprises computer instructions to insert default information for missing data into the calculator input set to form a resulting calculator input set using:
      (i) a library of expected physical pipeline attributes;

(ii) a library of pipeline location information; and
(iii) a library of testing information for pipelines;
g. performing an MAOP or MOP calculation on a record by record basis using the resulting calculator input set forming a MAOP or MOP output set, wherein the MAOP or MOP calculations are performed using the processor in communication with the non-transitory computer readable medium, wherein the non-transitory computer readable medium further comprises computer instructions to calculate record by record MAOP or MOP on the resulting calculator input set forming a MAOP or MOP output set;
h. showing valid and invalid MAOP or MOP calculations for the MAOP or MOP output set using both (i) graphically valid and invalid MAOP calculations or MOP calculations and (ii) a listing of valid and invalid MAOP calculations or MOP calculations using an executive dashboard viewable 24 hours a day, 7 days a week from a plurality of client devices simultaneously via a network using the processor in communication with the non-transitory computer readable medium, wherein the non-transitory computer readable medium further comprises computer instructions to: (i) graphically depict valid and invalid MAOP calculations or MOP calculations, (ii) provide a listing of valid and invalid MAOP calculations or MOP calculations using an executive dashboard viewable 24 hours a day, 7 days a week from a plurality of client devices simultaneously via a network; and
i. wherein the invalid MAOP calculations are presented as a value less than an established MAOP or MOP and the valid MAOP or MOP calculations are presented as a value equal to or greater than an established MAOP or MOP calculation.

2. The method of claim 1, wherein the gaps in MAOP data or MOP data are identified visually using graphs and colors to depict the missing data and gaps.

3. The method of claim 1, wherein the MAOP or MOP output set are identified in customized reports, standard reports, exception reports, Route MAOP Summary report, and reports required for regulatory filing.

4. The method of claim 1, wherein the MAOP or MOP output set is sorted and viewed by numerical data quality.

5. The method of claim 4, wherein any one piece of data is edited before MAOP or MOP calculation is performed.

6. The method of claim 1, further comprising creating multiple user accounts per pipeline operator.

7. The method of claim 1, further comprising using multiple formats of authenticated and non-authenticated data.

8. The method of claim 1, further comprising using an encryption module controlling access to the MAOP or MOP output set.

9. The method of claim 1, wherein the information is maintained in a cloud based server.

10. The method of claim 1, wherein a user manually inserts a default value into the MAOP or MOP input data.

11. The method of claim 1, further comprising creating an auditable trace between authenticated MAOP or MOP input data and the source documents using a unique identifier.

12. The method of claim 1, further comprising providing government regulatory citations that were used to form the MAOP or MOP output set.

13. The method of claim 1, further comprising providing a report to a user of a major discrepancy with MAOP or MOP output set compared to a pipeline operator established MAOP or MOP.

14. The method of claim 1, further comprising using the MAOP or MOP outset set to determine if a pipeline is capable of a higher operating pressure rating than currently been established.

15. The method of claim 1, further comprising sorting the collected information of the pipeline data sets for duplicates or for older superseded information and deactivating the duplicates and older information prior to performing dynamic segmentation.

* * * * *